United States Patent [19]
Schultz et al.

[11] Patent Number: 5,899,201
[45] Date of Patent: May 4, 1999

[54] AEROSOL ACTUATOR

[75] Inventors: Robert K. Schultz, Edina, Minn.; Constantinos Sioutas, Boston, Mass.

[73] Assignee: Minnesota Mining and Manufacturing Company, St. Paul, Minn.

[21] Appl. No.: 08/067,221

[22] Filed: May 26, 1993

[51] Int. Cl.⁶ .............................................. A61M 11/00
[52] U.S. Cl. ............................. 128/200.23; 128/200.14; 128/200.18
[58] Field of Search .................. 128/200.14, 200.18, 128/200.23, 203.15

[56] References Cited

U.S. PATENT DOCUMENTS

| | | | |
|---|---|---|---|
| 3,653,380 | 4/1972 | Hansen | 128/203.15 |
| 3,897,779 | 8/1975 | Hansen | 128/203.15 |
| 4,484,577 | 11/1984 | Sackner et al. | 128/200.23 |
| 4,570,630 | 2/1986 | Elliott et al. | 128/203.15 |
| 4,576,157 | 3/1986 | Raghuprasad | 128/203.15 |
| 4,664,107 | 5/1987 | Wass | 128/200.23 |
| 4,852,561 | 8/1989 | Sperry | 128/200.23 |
| 4,940,051 | 7/1990 | Lankinen | 128/203.15 |
| 5,048,729 | 9/1991 | Pritchard | 222/402.1 |
| 5,115,803 | 5/1992 | Sioutas | 128/200.23 |

FOREIGN PATENT DOCUMENTS

| | | |
|---|---|---|
| 71408/74 | 7/1974 | Australia . |
| 61599/90 | 4/1991 | Australia . |
| 9202198 | 7/1992 | Germany . |
| 92/05825 | 4/1992 | WIPO . |
| 93/04718 | 3/1993 | WIPO . |

*Primary Examiner*—Aaron J. Lewis
*Attorney, Agent, or Firm*—Ted K. Ringsred; MarySusan Howard; Robert W. Sprague

[57] ABSTRACT

A hand held aerosol actuator involving an aerosol source and a chamber having walls defining a constriction aperture. The aerosol source communicates with the chamber and directs an aerosol dose along an axis into the chamber. The constriction aperture is coaxial with the exit orifice and is dimensioned such that the respirable mass of the aerosol dose is increased relative to the respirable mass of an aerosol dose expelled through a like actuator not having the constriction aperture.

9 Claims, 1 Drawing Sheet

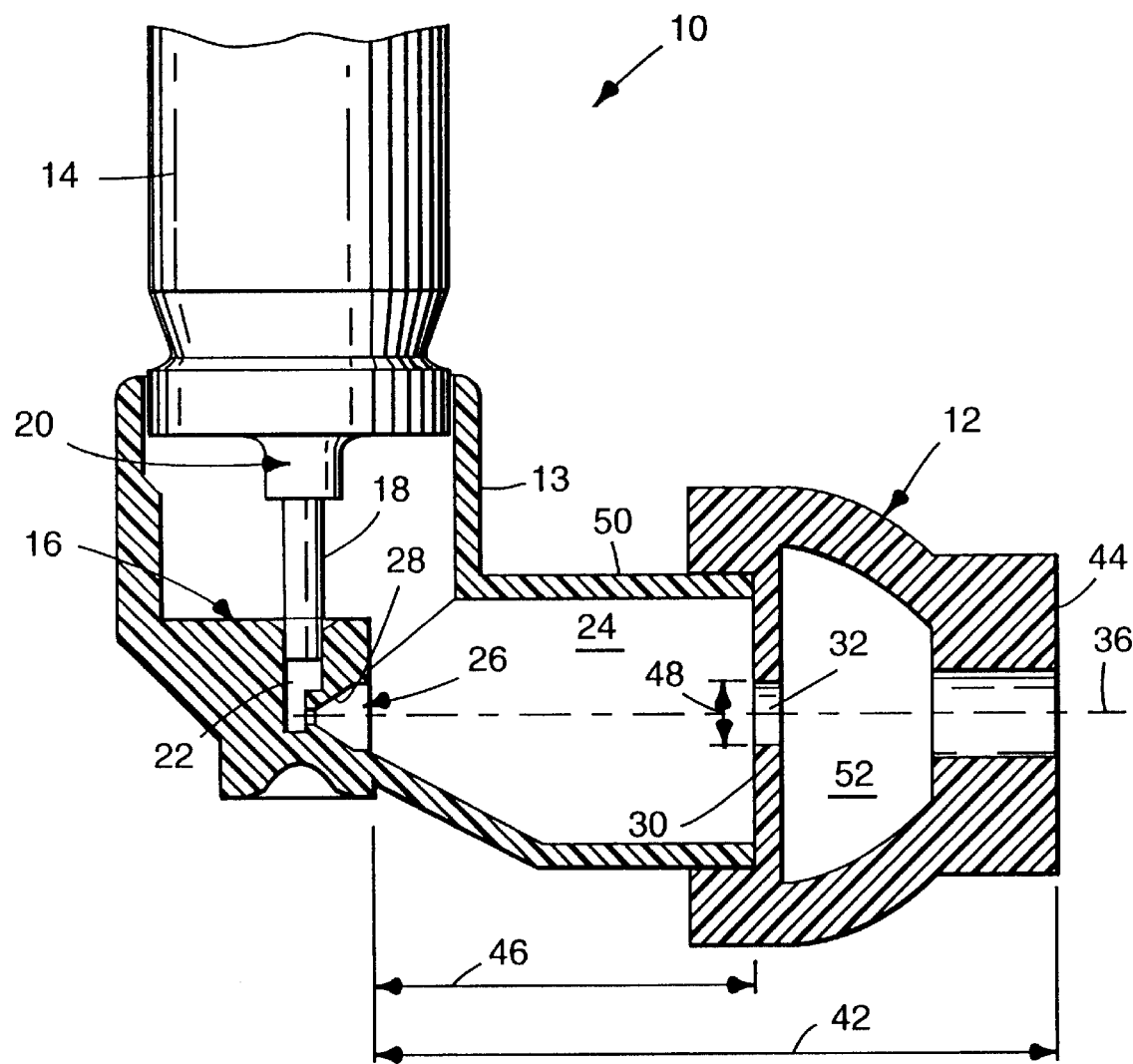

AEROSOL ACTUATOR

BACKGROUND OF THE INVENTION

1. Field of the Invention

This invention relates to actuators for use in connection with medicinal aerosol formulations.

2. Description of the Related Art

Pulmonary disorders such as asthma, chronic bronchitis, emphysema, and chronic obstructive pulmonary disease are often treated with drugs contained in medicinal aerosol formulations. Such formulations are commonly delivered using a metered dose inhaler ("MDI") that is designed to expel a dose of the drug in a form that can be inhaled into the lung, where the drug can exert its desired local therapeutic effect. With MDIs involving propellant based formulations the dose is expelled at a high velocity and in the form of particles or droplets from which the propellant preferably evaporates prior to inhalation. With many such MDIs a significant fraction of the expelled dose does not reach the lung; rather it is deposited in the mouth, the throat, or the upper airways where it is not therapeutically effective.

The turbulent nature of the fluid flow in an aerosol actuator when taken together with the presence of particles (and the variable size of such particles) in the aerosol dose makes difficult the design of improved actuators. Devices have been designed to increase the fraction of the expelled dose that can reach the lungs. Spacers, which allow the expelled dose to decelerate and allow time for evaporation of propellant, have been used to some advantage. These devices, however, are rather large and relatively inconvenient. U.S. Pat. No. 5,115,803 (Sioutas) describes a device that uses the energy of the expelled dose to create shear forces that break up particle agglomerates, thereby increasing the fraction of the drug that is present in the form of particles of respirable size. This device also decelerates the particles such that they are present in the form of a cloud that can be inhaled. Other problems have been addressed through actuator design. For example, U.S. Pat. No. 5,048,729 (Pritchard) describes an aerosol dispenser involving an applicator that includes a frustoconical diverter with a small orifice of diameter 0.5 mm facing a valve orifice. Aerosol droplets are said to predominantly pass through the orifice, decelerate, and be inhaled, while the propellant gas is predominantly diverted out of the dispenser.

SUMMARY OF THE INVENTION

This invention provides a hand held aerosol actuator, comprising:

an aerosol source capable of expelling a turbulent aerosol dose of drug comprising particles of respirable size and a chamber having walls defining a constriction aperture; wherein the aerosol source communicates with the chamber and comprises an exit orifice that directs the aerosol dose along an axis into the chamber, the walls defining the constriction aperture are opposite the exit orifice, and the constriction aperture is coaxial with the exit orifice and has a cross sectional area of about 0.20 cm$^2$ to about 0.60 cm$^2$.

In another aspect this invention provides a hand held aerosol actuator comprising an aerosol source as defined above and a chamber comprising walls defining a constriction aperture, wherein the aerosol source communicates with the chamber and comprises an exit orifice that directs the aerosol dose along an axis into the chamber, the walls defining the constriction aperture are opposite the exit orifice and either normal to said axis or convex to the exit orifice, and wherein the constriction aperture is coaxial with the exit orifice and dimensioned such that the respirable mass of the aerosol dose is increased relative to the respirable mass of an aerosol dose expelled through a like actuator not having the walls defining the constriction aperture.

Compared to a conventional actuator, an actuator of the invention is capable of delivering a dose of drug in the form of an aerosol such that more drug reaches the area of the lung where it is therapeutically effective. Also less drug is deposited in the mouth and throat, thus decreasing undesired systemic effects of the drug.

BRIEF DESCRIPTION OF THE DRAWING

The Drawing is a cross sectional view of one embodiment of the invention intended for use in connection with a propellant based metered dose inhaler.

DETAILED DESCRIPTION OF THE INVENTION

An actuator of the invention comprises an aerosol source capable of expelling an aerosol dose of drug comprising particles of respirable size. The aerosol source is preferably based on a pressurized liquid propellant such as propellant 12 (dichlorodifluoromethane), propellant 21 (dichlorofluoromethane), propellant 114 (1,2-dichloro-1,1,2,2-tetrafluoroethane), propellant 114a (1,1-dichloro-1,1,2,2-tetrafluoroethane), propellant 142b (1-chloro-1,1-difluoroethane), propellant 152a (1,1,-difluoroethane), and mixtures thereof such as mixtures of propellant 114 and propellant 12. Also suitable are hydrocarbon propellants such as propane, isobutane, and butane, fluorocarbons such as octafluoropropane and octafluorocyclobutane, dimethyl ether, and non-CFC propellants such as hydrofluoroalkanes, e.g., propellant 134a (1,1,1,2-tetrafluoroethane) and propellant 227 (1,1,1,2,3,3,3-heptafluoropropane). Suitable aerosol sources include any such aerosol source that produces an aerosol dose involving turbulent fluid flow: pressurized aerosol canisters such as those involving a metered dose valve and containing a propellant based medicinal aerosol formulation, or such an aerosol canister in combination with an actuator through which the aerosol dose passes. Dry powder aerosol sources such as those using a source of compressed gas to expel a dose of drug from an exit orifice (e.g., the aerosol sources disclosed in Patent Application PCT/US92/07156 (Whaley et al., incorporated herein by reference)), pump spray nebulizers, and the like, may also find use as aerosol sources for use in connection with the claimed invention.

As used herein the term "particles of respirable size" means particles that have an average diameter of less than about 10 microns, preferably between about 2 and 5 microns. Typically a dose that is produced by an aerosol source such as those mentioned above will also contain some fraction of particles that are larger than respirable size and/or larger agglomerates comprising several individual particles of respirable size.

The aerosol source communicates with a chamber and comprises an exit orifice that directs the aerosol dose along an axis into the chamber. Such an exit orifice can be any orifice, opening, channel, or the like that serves to direct the aerosol dose into the chamber. The exit orifice can be integral with other components of the aerosol source (e.g., it can be the opening in a dose chamber in a dry powder aerosol source) or it can be comprised by a component of the aerosol source (e.g., it can be a channel through a nozzle block in a metered dose inhaler).

The chamber comprises walls defining a constriction aperture. The walls defining the constriction aperture are opposite the exit orifice of the aerosol source and can be disposed normal to the axis of the exit orifice, concave to the exit orifice, convex to the exit orifice, or in any other manner such that the chamber functions as an expansion chamber, decelerating the aerosol dose. The constriction aperture is coaxial with the exit orifice (i.e., the constriction aperture lies along the axis along which the aerosol dose is directed into the chamber). The distance between the exit orifice of the aerosol source and the constriction aperture is limited by the need for the chamber to function as an expansion chamber in which the aerosol dose decelerates. Suitable dimensions for the chamber can be readily selected by those skilled in the art. The distance between the exit orifice and the constriction aperture is preferably from about 1 cm to about 3 cm, the lesser dimension being limited by the need for the chamber to serve its intended function and the greater dimension being limited by the preference for a compact design.

In one embodiment of the invention the constriction aperture has a substantially circular cross section having an area of about 0.20 $cm^2$ to about 0.60 $cm^2$, preferably about 0.30 $cm^2$. It has been found that constriction apertures of this shape and size afford improved respirable mass (as determined by the Test Method set forth in detail below) compared to a like device that contains no walls defining a constriction aperture and compared to a like device containing a constriction aperture that is outside of the recited size range.

In another embodiment of the invention the walls defining the constriction aperture are disposed in a non-concave relationship to the exit orifice (e.g., they are normal to the axis of the exit orifice or convex to the exit orifice) and the constriction aperture is dimensioned such that the respirable mass of the aerosol dose is increased relative to the respirable mass of an aerosol dose expelled through a like actuator not having the walls defining the constriction aperture. Such dimension can be selected readily by those skilled in the art. The constriction aperture is preferably circular and preferably has a cross sectional area of about 0.20 $cm^2$ to about 0.60 $cm^2$, more preferably about 0.30 $cm^2$.

A preferred embodiment of the invention is illustrated in the Drawing, which illustrates an embodiment of the invention intended for use in connection with a propellant based metered dose inhaler. Actuator 10 is a hand held device comprising a mouthpiece 12 through which a patient can inhale an aerosolized metered dose of drug expelled from an aerosol canister that is held by housing 13.

Actuator 10 comprises housing 13 adapted to receive and support aerosol canister 14 containing a medicinal aerosol formulation. Nozzle block 16 is adapted to receive valve stem 18 of metered dose valve 20, which is affixed to aerosol canister 14. Nozzle block 16 comprises walls defining channel 22, which communicates between valve stem 18 and chamber 24. Channel 22 has an exit orifice 26 comprising frustoconical portion 28. The combination of aerosol canister 14, metered dose valve 20, and nozzle block 16 constitutes an aerosol source for the purposes of the specification and claims.

Exit orifice 26 can be any size and shape provided that the minimum diameter is suitable for passing the medicinal aerosol formulation into chamber 24. Common minimum diameters range from about 0.25 mm to about 0.64 mm. With conventional actuators wider diameters commonly are used in connection with suspension aerosol formulations. Narrower diameters commonly are used in connection with solution aerosol formulations and with suspension aerosol formulations that are particularly difficult to deliver in the form of an aerosol containing a high respirable mass. Exit orifices with narrow diameters, however, can cause undue backpressure in the nozzle block, resulting in undesired blowback of some of the formulation when the aerosol canister is actuated. It has been found that an actuator of the invention obviates the need for the use of narrow exit orifices.

Actuator 10 further comprises chamber 24 which has walls 30 defining constriction aperture 32. An aerosol dose is introduced to chamber 24 along axis 36 determined by configuration of the exit orifice. The dose decelerates and passes through aperture 32 into mouthpiece 12, in part by way of the force of the aerosol source and in part through inhalation by a patient.

The Drawing illustrates a two piece construction wherein the mouthpiece is separable from the housing. It is friction fit over walls 50 of housing 13. Integral actuators comprising a single molded element are preferred, particularly when they are constructed as relatively small units having a chamber 24 of the minimum length effective to allow it to function as an expansion chamber. The embodiment shown in the Drawing also comprises second chamber 52 between the constriction aperture and terminus 44 of the mouthpiece. This chamber is optional and as illustrated is generally frustoconical with the greatest radius generally proximal to the constriction aperture. The second chamber, if any, can be of any suitable shape, e.g., it can be generally cylindrical and of a radius greater than or equal to the radius of the constriction aperture, or it can be generally frustoconical with the greater radius relatively distal to the constriction aperture.

The embodiment of the invention that is illustrated in the Drawing requires the user to coordinate inhalation with manual actuation of an aerosol canister. An actuator of the invention can also comprise a breath actuation means for discharging a dose of drug. Such means (e.g., those disclosed in U.S. Pat. No. 4,664,107 (Wass)) can be readily incorporated into an actuator of the invention in order to eliminate the need for a user to coordinate inhalation with actuation.

The invention is further illustrated in the Examples that follow.

Referring to the Drawing, actuator 10 comprises a housing 13, nozzle block 16 having an exit orifice 26, a constriction aperture 32, and a mouthpiece 12. Actuators were prepared having walls 50 of varying length in order to vary length 42 from the exit orifice to terminus 44 of the mouthpiece and distance 46 from the exit orifice to walls 30 defining the constriction aperture. Several mouthpieces were made, each with a particular radius 48 of the constriction aperture. The several dimensions are shown in Table 1.

The actuators described in Table 1, and a standard actuator not having a constriction aperture (substantially as shown in the Drawing but without mouthpiece 12), were tested with a suspension aerosol formulation containing 0.457 parts by weight pirbuterol acetate, 0.305 parts by weight sorbitan trioleate, 29.8 parts by weight propellant 11, and 69.438 parts by weight propellant 12. The formulation was contained in an aerosol canister equipped with a 50 microliter metered dose valve. All actuators had an exit orifice diameter of 0.56 mm.

Results were obtained according to the method set forth below:

RESPIRABLE FRACTION

In this assay the respirable fraction (the percent by weight of particles having an aerodynamic particle size of less than 4.7 microns) of the aerosol suspension is determined using an Anderson Cascade Impactor (available from Anderson Sampler Inc,; Atlanta, Ga.).

The aerosol vial to be tested is primed five times. The valve and valve stem are then cleaned with methanol and dried with compressed air. The aerosol vial and a clean, dry actuator are coupled to the glass throat attached to the top of the impactor using an appropriate firing adaptor. The calibrated vacuum pump (28.3 L/min) attached to the cascade impactor is turned on. A total of 10–20 sprays is delivered into the cascade impactor by repeatedly shaking the vial, seating it in the actuator and immediately delivering a single spray. The time between sprays is approximately 10 seconds. The cascade impactor is disassembled, the glass throat and each component is rinsed separately with an appropriate solvent. Each solution is analyzed for drug content to determine the amount of drug on each component and the total amount of drug delivered. The respirable mass is the amount of drug recovered from plates 3–7. Respirable fraction is calculated as follows:

$$\% \text{ respirable} = \frac{\text{respirable mass}}{\text{total drug} - \text{drug recovered from actuator and valve}} \times 100$$

Results are set forth in Table 1 below, wherein each entry is the average of at least 2 independent determinations.

TABLE 1

| Actuator | Radius 48 (cm) | Length 42 (cm) | Distance 46 (cm) | Respirable Mass (Mg/Shot) | Respirable Fraction (%) | Amount Retained on Throat (Mg/Shot) | Total Drug (Mg/Shot) |
|---|---|---|---|---|---|---|---|
| Standard Actuator | | | | 71.4 | 36.5 | 105.2 | 266.3 |
| 1 | 0.318 | 2.54 | 1.13 | 107.4 | 68.8 | 31.9 | 254.7 |
| 2 | 0.318 | 2.79 | 1.25 | 104.5 | 70.6 | 28.2 | 233.7 |
| 3 | 0.318 | 3.05 | 1.51 | 109.6 | 70.1 | 25.7 | 264.6 |
| 4 | 0.318 | 3.81 | 1.13 | 113.8 | 73.4 | 24.9 | 251.4 |
| 5 | 0.318 | 4.06 | 1.25 | 102.7 | 69.0 | 27.0 | 277.2 |
| 6 | 0.318 | 4.32 | 1.51 | 109.7 | 68.5 | 27.2 | 264.9 |
| 7 | 0.318 | 6.35 | 2.27 | 93.9 | 67.0 | 32.4 | 247.9 |
| C-1 | 0.159 | 2.54 | 1.13 | 71.0 | 61.8 | 37.4 | 249.7 |
| C-2 | 0.159 | 2.79 | 1.25 | 58.9 | 66.2 | 25.3 | 255.6 |
| C-3 | 0.159 | 3.05 | 1.51 | 63.0 | 67.3 | 25.0 | 262.6 |
| C-4 | 0.159 | 3.30 | 1.76 | 67.9 | 53.0 | 46.7 | 280.0 |
| C-5 | 0.635 | 4.06 | 2.27 | 71.2 | 64.3 | 26.4 | 253.3 |
| C-6 | 0.635 | 5.08 | 2.27 | 69.3 | 75.4 | 12.7 | 250.4 |
| C-7 | 0.635 | 6.35 | 2.27 | 68.8 | 82.0 | 5.3 | 249.4 |

The results in Table 1 show that an actuator of the invention provides an improvement in respirable mass compared to a commercially available actuator having no constriction aperture. The results also show that the size of the constriction aperture is responsible for the improvement, but length 42 and distance 46 are not unduly critical to the function of an actuator of the invention.

Actuator 1 from Table 1, a like actuator having an exit orifice diameter of 0.254 mm (designated Actuator 8), a standard suspension actuator having an exit orifice diameter of 0.56 mm (Model M3710, 3M), and a standard solution actuator having an exit orifice diameter of 0.254 mm (Model M3756, 3M) were tested with a solution aerosol formulation containing 0.43 parts by weight beclomethasone dipropionate, 12 parts by weight ethanol, and 87.57 parts by weight 1,1,1,2-tetrafluoroethane. Results are shown in Table 2 below.

TABLE 2

| Actuator | Respirable Fraction (%) | Respirable Mass (µg/Shot) | % Retained on Throat |
|---|---|---|---|
| Standard Suspension (M3710) | 46 | 71 | 50 |
| Standard Solution (M3756) | 62 | 85 | 34 |
| 1 | 76 | 86 | 22 |
| 8 | 62 | 98 | 36 |

The results in Table 2 show that an actuator of the invention having a conventional suspension formulation exit orifice delivers a solution formulation with a higher respirable fraction and a lower percentage retained on the throat than the other tested actuators, including those having an exit orifice designed for use in connection with solution formulations. Good respirable mass was achieved with both actuators of the invention.

Actuator 1, along with a standard suspension actuator (Model M3710, 3M) and a standard solution actuator (Model M3756, 3M), was tested with a formulation containing pirbuterol acetate (0.9 percent by weight) in 1,1,1, 2,3,3,3-heptafluoropropane (Formulation A) or a formulation containing pirbuterol acetate (0.9 percent by weight), ethanol (10 percent by weight), oleic acid (0.5 percent by weight), and 1,1,1,2,3,3,3-heptafluoropropane (Formulation B). Results are shown in Table 3 below.

TABLE 3

| Formulation | Actuator | Respirable Fraction (%) | Respirable Mass (µg/Shot) | % Retained on Throat |
|---|---|---|---|---|
| B | Standard Suspension | 16% | 38.1 | 64 |
| B | 1 | 45 | 80 | 24 |
| A | Standard Solution | 34 | 73 | 47 |
| A | 1 | 63 | 104 | 15 |

The results in Table 3 show that the actuator of the invention provides higher respirable mass with less drug retention on the throat than the conventional actuator when used with the tested formulations.

What is claimed is:

1. A hand held aerosol actuator, comprising:

an aerosol source capable of expelling a turbulent aerosol dose of drug comprising particles of respirable size and a chamber having walls defining a constriction aperture; wherein the aerosol source communicates with the chamber and comprises an exit orifice that directs the aerosol dose along an axis into the chamber, the walls defining the constriction aperture are opposite the exit orifice, and the constriction aperture is coaxial with the exit orifice and has a cross sectional area of 0.20 cm$^2$ to 0.60 cm$^2$.

2. An actuator according to claim 1, wherein the aerosol source comprises a pressurize aerosol canister comprising an aerosol valve.

3. An actuator according to claim 2, wherein the pressurized aerosol canister comprises a metered dose aerosol valve and contains a propellant based medicinal aerosol formulation.

4. An actuator according to claim 1, wherein the aerosol source comprises: a pressurized aerosol canister comprising an aerosol valve, in combination with a nozzle block defining said exit orifice.

5. An actuator according to claim 1, wherein the aerosol source comprises means for producing a dry powder aerosol.

6. An actuator according to claim 1, wherein the aerosol source is a dry powder aerosol source using a source of compressed gas to expel a dose of drug from an exit orifice.

7. An actuator according to claim 1, wherein the constriction aperture has a cross sectional area of about 0.30 cm$^2$.

8. An actuator according to claim 1, wherein the constriction aperture has a circular cross section.

9. An actuator according to claim 1, wherein the walls defining the constriction aperture are comprised by a separable mouthpiece.

* * * * *